United States Patent [19]

Guth et al.

[11] Patent Number: 4,982,046
[45] Date of Patent: Jan. 1, 1991

[54] OLEFIN OLIGOMERIZATION

[75] Inventors: Jean-Louis Guth; Anne-Catherine Faust, both of Mulhouse; Francis Raatz, Rueil-Malmaison, all of France

[73] Assignee: Institut Francais Du Petrole, Rueil-Malmaison, France

[21] Appl. No.: 372,599

[22] Filed: Jun. 28, 1989

Related U.S. Application Data

[62] Division of Ser. No. 124,122, Nov. 23, 1987, Pat. No. 4,853,203.

[30] Foreign Application Priority Data

Nov. 21, 1987 [FR] France ................. 86 16362

[51] Int. Cl.$^5$ .............. C07C 2/00; C07C 2/12
[52] U.S. Cl. ............... 585/533; 585/525; 585/520; 585/530
[58] Field of Search ......... 585/533, 525, 520, 530; 423/328, 326

[56] References Cited

U.S. PATENT DOCUMENTS 3,515,769  6/1970  Fishel ........................... 585/533
4,596,704  6/1986  Miale et al. .................. 423/328 C
4,788,374 11/1988  Chu et al. .................... 585/533
4,853,203  8/1989  Guth et al. ................... 423/328

FOREIGN PATENT DOCUMENTS 0055529  7/1982  European Pat. Off. ........ 423/328 T

*Primary Examiner*—Chung K. Pak
*Attorney, Agent, or Firm*—Millen, White and Zelano

[57] ABSTRACT

Olefin oligomerization employing as a catalyst
(a) a ferrierite of the following approximate formula:

$$M_{x/n}(T^{III}O_2)_x(Si^{IV}O_2)_{36-x}$$

where
$T^{III}$ represents at least one element selected from the group of boron ($B^{III}$), aluminum ($Al^{III}$), gallium ($Ga^{III}$) and iron ($Fe^{III}$);
x ranges from 0.05 to 6.6;
M is a compensation cation; and
n is the valence of M;
(b) an X-ray diffraction diagram shown in Table 1 of the description;
(c) a fluorine content after synthesis ranging from about 0.01 to 1.6% by weight; and
(d) a $Si^{IV}/T^{III}$ molar ratio of at least about 4.75.

9 Claims, No Drawings

OLEFIN OLIGOMERIZATION

This is a division of application Ser. No. 124,122, filed Nov. 23, 1987, now U.S. Pat. No. 4,853,203.

The present invention concerns olefin oligomerization utilizing ferrierites as catalysts.

BACKGROUND OF THE INVENTION

Ferrierite is a natural zeolite of the approximate formula: $(Na,Mg)_{x/3}(AlO_2)_x(SiO_2)_{36-x}8H_2O$ characterized by a value of x close to 6. The structure of a crystallized zeolite is formed of a frame resulting from the linking of $TO_{4/2}$ tetrahedrons, each oxygen being common to two tetrahedrons. T is mostly silicon or aluminum, but other trivalent elements such as boron, gallium or iron may be introduced instead of aluminum into $TO_4$ tetrahedons of the frame of certain zeolites. The presence of these trivalent elements, together with tetravalent silicon, gives negative charges to the frame, said charges being neutralized by compensation cations. The microporous volume left free by the frame is occupied by exchangeable compensation cations and different chemical species such as water, amines, alcohols, salts, bases etc. It is important to observe that all these species, by their introduction during the zeolite formation, are responsible for its microporous structure. As a matter of fact, by their shape, their size and their interactions, they make it possible to build light frames comprising voids of variable volume and shape.

The use of zeolites as microporous solids for selective adsorption or for catalysis requires at least a partial removal by heating or roasting of the species introduced during the synthesis. Each type of zeolite has then a distinct microporous structure related with the geometry of the frame and with the number and the size of the present compensation cations. The variation in size and shape of the channels and recesses from one type to the other results in changes of the adsorbing properties. Only the molecules having certain sizes and shapes are capable to penetrate the pores of a given zeolite. In view of these remarkable characteristics, zeolites are particularly convenient for the purification or separation of gas or liquid mixtures such for example as hydrocarbons separation by selective adsorption.

The chemical composition with the nature of the elements present in the $TO_{4/2}$ tetrahedrons and the nature of the compensation cations is also an important factor having an effect on the selectivity of adsorption and mainly on the catalytic activity of these products. This is explained by the nature and the intensity of the interactions between zeolites and the molecules adsorbed on their internal surface. They are used as catalyst carriers or catalysts for cracking and modifying hydrocarbons as well as in the preparation of many molecules.

Among these different types of zeolites for industrial use in separation or catalytic processes, ferrierite is very using. With a relatively high Si/Al ratio, its structure has a high stability. For the same reasons, it has a strong acidity when the compensation cations are $H^+$ protons and its stability remains acceptable. Finally, the geometry of its microporous system and the size of the micropores ($4.3 \times 5.5$ A in the direction (001) and $3.4 \times 4.8$ A in the direction (010) with interconnection of the two channel systems) provides a microporous solid having a good selectivity in adsorption and catalysis operations.

Fields of natural ferrierites are known, but the industrial use of these products is limited by the variable quality of the products and the presence of impurities forming undesirable charges in certain processes. On the other hand, some applications require higher Si/Al ratios than that of natural ferrierites, which range from 4 to 7. As a rule, it is of course possible to increase this ratio by different chemical treatments but these processes are time-consuming and costly. On the other hand, dealumination of ferrierite by post synthesis treatments known in the prior art has proved to be very difficult, or even impossible (G. FERRE, Doctor-Engineer Thesis, ENSPM 1986).

These problems have initiated substantial research in an effort synthesize ferrierites having the desired qualities and properties. These syntheses are disclosed in many patents and papers, such for example as paper of R. M. BARRER and D. J. MARSHALL (J. Chem. Soc. 1964 p. 485) and the following patents: FR No. 2 228 721 (1974); U.S. Pat. No. 3,966,883 (1976); Ger offen No. 2 548 697 (1976); U.S. Pat. No. 3,933,974 (1976); U.S. Pat. No. 4,016,245 (1977); U.S. Pat. No. 4,017,590 (1977); U.S. Pat. No. 4,088,739 (1978); EP No. 12 473 (1980); U.S. Pat. No. 4,259,306 (1982); EP No. 55 529 (1982); EP No. 49 386 (1982); JP No. 5 973 423 (1984); JP No. 6 019 1017 (1985); JP No. 6 014 1617 (1985).

The synthetic ferrierites disclosed in the literature are all prepared by hydrothermal treatment of a basic aqueous medium containing a silica and alumina source. In order to obtain the basic pH($>10$) necessary for dissolving the silica and alumina sources and for zeolite crystallization one or more inorganic bases as NaOH and(or) alkaline silicates and aluminates are generally used. Quaternary amines or ammonium are often associated to said bases in order to direct the gel crystallization towards ferrierite and to favor an increase of the Si/Al ratio in the zeolite, as illustrated by U.S. Pat. Nos. 4,046,859 and 4,107,195.

This procedure suffers from several disadvantages. The zeolites having a light structure as does ferrierite are generally metastable in their basic formation medium and accordingly are difficult to obtain in a very pure state. They are often accompanied with heavier and more stable phases. This difficulty increases with the amount of product to prepared, prepare, i.e. when passing from the laboratory scale to the industrial scale.

On the other hand, these basic media are not favorable to the crystallization of phases of very high silica content. As a matter of fact, it is well known that the pH increase in the synthesis medium results in a decrease of the Si/Al ratio in the zeolite which crystallizes. In this connection, the solubility in basic media increases with the Si/Al ratio, is, the effect being a reduced yield of the preparations. The metastability of the zeolites requires very highly oversaturated media to obtain their crystallization, thus producing a quick nucleation to the prejudice of the crystal growth, thereby resulting generally in crystals of small size.

Many applications of ferrierite, particularly in acid catalysis, require zeolite in protonated form and entirely freed from its alkaline cations introduced as compensation cations during the synthesis. This can be achieved by processes of repeated and extended ion exchange with $NH_4^+$ cations followed by roasting to decompose them to $H^+$ cations. This ion exchange step could be omitted if it were possible to replace the alkali cations by $NH_4^+$ cations during the synthesis. But this is not possible when the pH is higher than about 10, NH$_4^+$ being in these conditions converted to NH$_3$. On the other hand, the synthesis conducted at pH values for which NH$_4^+$ is stable, are difficult and time-consuming in view of the low solubility of the silica and alumina sources at these low pH values.

SUMMARY OF THE INVENTION

The invention has as an object a synthetic ferrierite of the following approximate chemical formula:

$$M_{x/n}(T^{III}O_2)_x(Si^{IV}O_2)_{36-x}$$

wherein $T^{III}$ represents at least one element selected from the group of boron ($B^{III}$), aluminum ($Al^{III}$), gallium ($Ga^{III}$) and iron ($Fe^{III}$), x ranges from about 0.05 to 6.6

M is a proton resulting from the thermal decomposition of nitrogenous cations and/or at least one undercomposable cation originating from the reaction medium, for example a cation of alkali, alkaline earth metals, transition metals or other metals as specified hereinafter and/or a cation introduced by ion exchange processes.

n is the valence of M.

The ferrierite according to the present invention is also characterized by:

a X-ray diffraction diagram as reported in table 1, a fluorine content ranging from about 0.01% to 1.6% by weight, a $Si^{IV}/T^{III}$ molar ratio at least equal to about 4.75 and at most equal to about 700.

The new ferrierite compositions according to the invention have a $Si^{IV}/T^{III}$ molar ratio preferably ranging from 7 to 500, more preferably from 20 to 300 and a fluorine content preferably ranging from 0.20 to 1.0% by weight.

The presence of fluorine in the ferrierite according to the present invention modifies in particular its catalytic properties and provides solids whose performance is different from those known in the prior art.

When metal or alkaline-earth cations are introduced during the synthesis these ions may be easily removed by conventional ion-exchange operations and replaced, either directly (H$^+$) or indirectly (NH$_4^+$) by protons.

In use it is desirable to keep fluorine within the solid but, if necessary, a part of fluorine may be removed. Fluorine removal may be achieved by treating for several hours in an autoclave, between 100° and 200° C., the ferrierite in an ammonia diluted solution (ratio of solution volume to the solid weight ranging from 5 to 20 cm$^3$g$^{-1}$).

The invention also has as an object a new process for preparing zeolite of ferrierite type no longer suffering from the above-described disadvantages (particularly low Si/Al ratios, compulsory presence of undecomposable cations). According to this new process, the syntheses are conducted in aqueous medium having a pH lower than about 10 and containing fluoride anions. The latter replace the OH$^-$ anions of the conventional basic media and provide for the collection in the aqueous phase of the different elements which include silicon taking place into the TO$_{4/2}$ tetrahedrons of the frame. The new synthesis process is characterized by the steps of:

preparing a reaction mixture solution at a pH lower than about 10, mainly comprising water, a source of silicon oxide, a source of at least one oxide of trivalent metal T selected from the group consisting of boron, gallium, aluminum and iron, a source of fluoride ions F$^-$ and a source of at least one structurizing agent supplying nitrogen-containing organic cations. The structurizing agent is selected from primary or secondary linear aliphatic monoamines, diamines, triamines and ammonium cations derived by protonation of said amines, said agent having a total number of carbon and nitrogen atoms (C-N) from 3 to 8 and preferably from 3 to 5. Said mixture has a composition in terms of molar ratios ranging within the following intervals:

| | |
|---|---|
| $Si^{IV}/\Sigma T^{III}$: | 2–400 ($T^{III}$ = B, Al, Ga, Fe) |
| $F^-/Si^{IV}$: | 0.1–3 |

Organic structurizing agent/$Si^{IV}$: 0.1–4

$H_2O/Si^{IV}$: 4–200 heating said mixture to a temperature at most equal to 270° C., advantageously from 120° to 260° C. and preferably from 150° to 240° C., for a sufficient time to obtain ferrierite crystals, and roasting said crystals at a temperature higher than 400° C., and preferably ranging from 500° to 600° C. The roasting step as an object the removal of the organic or ammonium cations contained in the raw synthesis solid.

Ferrierites in H$^+$ form are thus obtained by mere roasting of the resultant synthesis products. These acid ferrierites may be used as such in many catalytic processes using solid acid catalysts, or they can be very easily exchanged with all the elements giving an aqueous solution of stable cations, such for example as Pt$^{2+}$, Fe$^{2+}$, Fe$^{3+}$, rare earth cations etc. . . .

In the synthesis step, it is preferred to proceed at a pH ranging from 3.5 to 10. Excellent results have been obtained, in particular with ferrierites having a very high ratio of silica to metal T oxide either with aluminum, boron, gallium or iron, alone or as associations thereof, when the pH was from about 4.5 to 9.

In the initial reaction medium in aqueous solution, it is preferred to select a composition whose molar ratios are within the following ranges:

| | |
|---|---|
| $Si^{IV}/\Sigma T^{III}$: | 4–150 ($T^{III}$ = B, Al, Ga, Fe) |
| $F^-/Si^{IV}$: | 0.25–2.5 |
| Organic structurizing agent/$Si^{IV}$: | 0.25–2.5 |
| $H_2O/Si^{IV}$: | 6–80 |

After the roasting step it is possible to introduce into the ferrierites, by well-known ion exchange methods, at least one element of the periodic classification whose cations may be prepared in aqueous medium and selected from the group formed of groups II$_A$, III$_A$, IV$_A$, I$_B$, II$_B$, III$_B$, IV$_B$, VI$_B$ and VIII of the periodic classification of elements.

Examples of such cations are alkali metal and metal cations, rare-earth cations, Fe$^{II}$, Fe$^{III}$, Co$^{II}$, Co$^{III}$, Ni$^{II}$, Zn$^{II}$, Ag$^+$.

Other structurizing agents than those mentioned above may be used, as known in the prior art, particularly compounds having amine, keto or, acid groups, for example amino-alcohols, amino-acids, polyalcohols or tertiary amines. Preferred amines are: C$_2$H$_5$—NH$_2$, nC$_3$H$_7$—NH$_2$, nC$_4$H$_9$—NH$_2$, NH$_2$—(CH)$_2$—NH$_2$, NH$_2$—(CH$_2$)$_3$—NH$_2$, (CH$_3$)$_2$NH, (C$_2$H$_5$)$_2$NH,

CH₃—NH—C₂H₅, CH₃—NH—C₃H₇, NH₂CH₂NH—CH₃, NH₂—CH₂—NH—CH₂—NH₂.

Examples of $Si^{IV}$ element sources to be used are silicas which are hydrogels, aerogels, colloidal suspensions, silicas resulting from the precipitation of soluble silicate solutions or from hydrolysis of silicic such as $Si(OC_2H_5)_4$ or complexes such as $(NH_4)_2SiF_6$, silicas prepared by extraction of natural or synthetic compounds such as aluminum silicates, aluminosilicates or, clays. Silica may also be introduced as soluble alkali silicates or solution thereof.

Examples of $B^{III}$ element sources to be used are boric acid $H_3BO_3$ or boric anhydride $B_2O_3$, as well as salts as borax, ammonium tetraborate or hydrolysable molecules such as $BF_3$, $BCl_3$ and esters of boric acid, such as triethylborate.

Examples of $Al^{III}$ element sources to be used are aluminum salts (for example sulfate, nitrate, chloride, fluoride, acetate), hydroxides, hydroxyoxides and aluminum oxides, aluminates, esters such as aluminum tripropylic ester $Al(OC_3H_7)_3$.

Examples of $Ga^{III}$ element sources to be used are gallium salts (for example sulfate, nitrate, chloride, fluoride, acetate), gallium hydroxides, hydroxyoxides and oxides, gallates and different esters.

Examples of $Fe^{III}$ element sources to be used are salts of trivalent iron (for example sulfate, nitrate, chloride, fluoride, acetate) ferric hydroxides, hydroxyoxides and oxides.

Instead of using separate sources of the different elements it is also possible to use sources where $Si^{IV}$ element is combined with one or more elements of the $B^{III}$, $Al^{III}$, $Ga^{III}$ and $Fe^{III}$ series as well as sources the two or more elements of the latter series are associated, such for example as silica alumina gel, borosilicate glass, gallium or aluminum mixed oxides or hydroxides.

The different T element sources of the $TO_{4/2}$ tetrahedrons of the frame may be engaged as solutions, gels of crystalline solids but also as aggregates such as extrudates or pellets which will then be converted to already conglomerated ferrierite.

The ammonium cations deriving from amines $(C,N)_{3-8}$ and preferably $(C,N)_{3-5}$ necessary for the ferrierite crystallization are added to the reaction medium as one of their salts such for example as n-propylammonium or n-butyl-ammonium chlorhydrates or fluorhydrate. The one or more optionally added amines $(C,N)_{3-8}$ will then be converted in situ to cations during the pH adjustment to a value lower than 10.

Fluoride anions are added as hydrofluoric acid or alkali metal fluorides, for example sodium fluoride, ammonium fluoride $NH_4F$, ammonium difluoride $NH_4HF_2$, hydrofluorides of amines $(C,N)_{3-8}$ or of hydrolyzable compounds which may release fluoride anions in water, as for example $SiF_4$ or $(NH_4)_2SiF_6$. Hydrofluoric acid, ammonium fluoride or ammonium difluoride are preferred since they are not expensive and they provide protonated ferrierites by mere roasting of the zeolite resulting from the synthesis.

The pH of the reaction medium is lower than 10, advantageously from 3.5 to 10 and more preferably from 4.5 to 9. It may be obtained either directly from one or more products as HF or $NH_4HF_2$ forming part of the reaction medium, or by adding to said medium an acid, a base, an acid salt, a basic salt or an additional buffer mixture.

The addition of ferrierite crystals (germs) to the reaction mixture in a proportion of at most 10% by weight with respect to the silica weight, generally facilitates the crystallization.

The reaction medium is preferably heated in an autoclave innerly coated with polytetrafluoroethylene (PTFE). According to the composition, the addition of germs, the temperature and the use of stirring or not, the heating lasts generally from 12 to 350 hours. When the crystallization is completed, the obtained solid is filtered and washed with dionized water.

The addition of germs and the stirring have also an effect on the size of the formed ferrierite crystals. By using these two factors, the size of the crystals may be varied from a few fractions of micron to a few hundred of microns. The crystals are generally shaped as small plates.

During the step of roasting crystals, the latter are heated in the presence of a gas, preferably dry and containing, when the crystals contain decomposable cations others than $NH_4^+$, preferably molecular oxygen. The roasting temperature is higher than 400° C. and ranges preferably from 500° to 600° C. so as to decompose the $NH_4^+$ and/or organic cations contained in the solid.

The products obtained by the process according to the invention are easily identified from their X-ray diffraction diagram which may be obtained by using a diffractometer and according to the powder method with copper radiation. From the position of the diffraction peaks, represented by angle $2\theta$, the characteristic reticular equidistances $\Delta d_{hkl}$ of the sample are calculated by the Bragg relationship. The estimation of the measuring error $\Delta d_{hkl}$ is calculated as a function of the error $\Delta 2\theta$ alloted to the measuring value $2\theta$ by the Bragg relationship. An error $\Delta 2\theta$ equal to $\pm 0.2°$ is currently accepted.

The relative intensity I/Io, wherein I is the intensity of a given line and Io the intensity of the stronger line, alloted to each $d_{hkl}$ value, is estimated from the height of the corresponding diffraction peak. Table 1 hereinafter reports the X-ray diffraction diagrams characterizing a ferrierite before roasting and a ferrierite roasted at 750° C. under argon, both products being obtained according to the invention. In the columns of $D_{hkl}$ are reported extreme values of the different equidistances of $d_{hkl}$. The values are dependent on the ratio $Si^{IV}/T^{III}$, on the nature of $T^{III}$ and on the nature of the compensation cations. Each of the values indicated in the table must further be corrected for the measuring error $\Delta d_{hkl}$. For characterizing the relative intensities I/Io, a symbol scale has been used: vl=very strong, s=strong, lm=medium to strong, m=medium, ml=medium to low, l=low, vs=very low, vvl=very very low. These relative intensities also depend partly on the ferrierite composition.

TABLE 1

| RX DIFFRACTION DIAGRAMS | | | |
|---|---|---|---|
| NON ROASTED FERRIERITE ACCORDING TO THE INVENTION A | | ROASTED FERRIERITE ACCORDING TO THE INVENTION B | |
| $d_{hkl}$ (Å) | I/Io | $d_{hkl}$ (Å) | I/Io |
| 11.10–11.40 | vl | 11.10–11.40 | vl |
| 9.20–9.50 | vs | 9.20–9.50 | vs |
| 7.55–7.80 | vvl | 7.55–7.80 | vvl |
| 6.95–7.20 | l | 6.95–7.20 | m |
| 6.85–7.10 | lm | 6.85–7.10 | m |
| 6.50–6.70 | l | 6.45–6.65 | lm |
| 6.05–6.25 | vl | | |
| 5.65–5.85 | l | 5.65–5.85 | l |
| 5.60–5.80 | l | 5.60–5.80 | lm |

TABLE 1-continued

RX DIFFRACTION DIAGRAMS

| NON ROASTED FERRIERITE ACCORDING TO THE INVENTION A | | ROASTED FERRIERITE ACCORDING TO THE INVENTION B | |
| --- | --- | --- | --- |
| $d_{hkl}$ (Å) | I/Io | $d_{hkl}$ (Å) | I/Io |
| 4.85–5.05 | vl | | |
| 4.72–4.88 | vl | 4.70–4.85 | l |
| 4.62–4.76 | vl | | |
| 3.90–4.02 | m | 3.90–4.02 | m |
| 3.84–3.95 | m | 3.84–3.95 | m |
| 3.78–3.89 | lm | 3.78–3.89 | lm |
| 3.72–3.83 | m | 3.72–3.83 | m |
| 3.54–3.70 | lm | 3.59–3.70 | lm |
| 3.48–3.58 | m | 3.48–3.58 | m |
| 3.40–3.50 | m | 3.40–3.50 | m |
| 3.31–3.41 | l | 3.31–3.41 | l |
| 3.26–3.35 | l | 3.26–3.35 | l |
| 3.02–3.16 | l (large) | 3.08–3.16 | lm |
| 2.99–3.07 | l | 2.99–3.07 | l |
| 2.90–2.98 | vl | 2.90–2.98 | l |
| 2.83–2.91 | vl | 2.84–2.92 | l |
| 2.79–2.86 | vl | 2.79–2.86 | vl |
| 2.66–2.74 | vl | 2.66–2.74 | l |
| 2.60–2.67 | vl | 2.60–2.67 | l |

The ferrierite according to the invention may be used as a catalyst, either pure or associated with a matrix containing compounds selected from the group consisting of alumina, silica, magnesia, zirconia, titanium oxide, boron oxide, a clay or any combination of at least two of the above-mentioned compounds. The ferrierite content of the catalyst will be at least 3% by weight, preferably at least 20%, and the matrix content will be at most 97% by weight and preferably at most 80%. Optionally, the catalyst may comprise a hydrogenating-dehydrogenating function brought by at least one metal, preferably selected from groups 1B and VIII or brought by at least one sulfide of metal selected from groups IB and VIII.

The ferrierites prepared according to the invention are used as catalyst or catalyst carrier, either pure or as mixture, in hydrocarbon conversion reactions and more particularly in the reaction of olefin oligomerization.

EXAMPLES

The following examples are given to illustrate the invention and must not be considered as limiting the scope thereof.

EXAMPLE 1

Preparation in fluoride medium of a ferrierite having a $SiO_2/Al_2O_3$ molar ratio of 40.

A sodium alumino-silicate sold under the Trademark "Tixolex 28" and previously treated with an aqueous acid solution, in order to increase the Si/Al ratio and to remove the $Na^+$ cations, is used as silica and alumina source. Accordingly, 350 g of Tixolex 28 is treated with 3.5 liters of $HNO_3(M/2)$ at room temperature for 3 hours, under stirring. The solid is then filtered, washed with water, dried at 60° C. and maintained over moistener. In the present and in the following examples this product is called "HNO3-treated Tixolex" and has the following composition: $SiO_2=77.5\%$, $Al_2O_3=5.2\%$, $Na_2O=0.15\%$, $H_2O=16.5\%$ ($SiO_2/Al_2O_3\approx25$).

9.24 g of HNO3-treated Tixolex are dispersed under stirring in a solution containing 23.9 g of $H_2O$, 9.73 g of 40% HF and 9.2 ml of n-propylamine. This reaction mixture, of PH 7, is then heated for 12 days at 170° C. in an autoclave lined with polytetrafluoroethylene (PTFE). After cooling the crystals present in a mother liquor of pH 7.5 are filtered, washed with water and then dried. Their size varies from 20 to 125 microns and the $SiO_2/Al_2O_3$ molar ratio, determined by chemical analysis after roasting in a 20% air and 80% $N_2$ mixture, at 550° C., is equal to 40. The crystals recovered have a X-ray diffraction diagram typical of ferrierite (see Table 1). No other phase is detected. The fluoride content of the raw synthesis solid is 0.78% by weight.

EXAMPLE 2

Preparation in fluoride medium of a ferrierite having a $SiO_2/Al_2O_3$ molar ratio of 30.

3.36 g of HNO3-treated Tixolex prepared according to example 1 are introduced under stirring into a solution containing 20.6 g of $H_2O$, 1.77 g of 40% HF and 3.33 ml of n-propylamine. After heating at 200° C. in autoclave lined with PTFE, crystals of about 40 μm are obtained, when 3 days have passed, in a mother liquor of pH 7 (measured after cooling). They are filtered, washed and dried. These crystals have the typical X-ray diffraction diagram of ferrierite, no other phase being detected. The chemical analysis performed after roasting in a 20% air and 80% $N_2$ mixture, at 550° C., gives a $SiO_2/Al_2O_3$ molar ratio close to 30. The fluoride content of the raw synthesis crystals is 0.65% by weight.

EXAMPLE 3

(comparative) Negative effect of inadequate $F^-$/Si and organic cation/$F^-$ ratios.

This example shows that $F^-$/Si and n-propylamine/Si too low molar ratios may lead to an incomplete crystallisation. With the same reactants as in example 2, a reaction mixture is formed which is characterized by a value of 0.05 of the two above-mentioned molar ratios. For this purpose, 4.2 g of HNO3-treated Tixolex (see example 1) are admixed with 0.62 ml of n-propylamine, 0.33 ml of 40% HF, 30 ml of $H_2O$ and 0.06 g of ferrierite crystals used as germs. The mixture, heated to 200° C. for 4 days, in an autoclave lined with PTFE gives, after filtration and washing, a solid containing only 15% of ferrierite (determination by X-ray diffraction)

EXAMPLE 4

(comparative) Negative effect of a too high pH value.

This example shows that a reaction mixture having a too high pH may lead to a ferrierite containing crystal impurities such as cristobalite.

A mixture is formed with a 5.04 g of HNO3-treated Tixolex (see example 1), 5 ml of n-propylamine, 1.71 g of $NH_4HF_2$ and 30 g of $H_2O$. The mixture, having a pH of 10.2, is heated to 200° C. for 4 days in an autoclave lined with PTFE. After cooling, the pH is 10.8 and the solid obtained after filtration and washing consists of a 40% ferrierite and 60% cristobalite mixture (determination by X-ray diffraction).

EXAMPLE 5

Preparation of ferrierites according to the invention from different organic cations.

Sodium alumino-silicate, sold under the trademark of "Tixolex 28", previously exchanged with $NH_4^+$ cations so as to remove $Na^+$ cations, is used as silica and alumina source. For this purpose, 250 g of Tixolex 28 are treated with 2.5 liters of $NH_4NO_3$ (M) for 16 hours at 60° C. After filtration and washing with water this treatment is repeated twice. After the last washing the product is dried at 60° C., then kept over moistener. It is composed of $SiO_2=73.5\%$, $Al_2O_3=8.7\%$, $Na_2O=0.2\%$, $(NH_4)_2O+H_2O=17.8\%$, the $SiO_2/Al_2O_3$ molar ration being 14.4. This source of silica and alumina is called: $NH_4{}^+$ exchanged Tixolex.

The four tests (5a, 5b, 5c and 5d) of this example are conducted with $NH_4{}^+$ exchanged Tixolex and with four different alkylammonium cations. The molar compositions of the reaction mixture for 1 mole of $SiO_2$ contained in $NH_4{}^+$ exchanged Tixolex and the synthesis conditions are indicated in Table 2.

In the four tests, after reaction in autoclave and separation of the mother liquors, ferrierite crystals are obtained whose diffraction spectra conform with the specifications of Table 1 (no other phase being detected by X-ray diffraction or microscopy). The mother liquors have pH values ranging from 6.5 to 9.0. The fluoride contents of the raw synthesis solids are respectively 0.54, 0.30, 0.40 and 0.60% by weight for samples 5a, 5b, 5c and 5d. After roasting at 550° C., the chemical analysis indicates respective $SiO_2/Al_2O_3$ molar ratio of 28, 22, 32 and 22 for samples 5a, 5b, 5c and 5d.

TABLE 2

| | Composition of the synthesis medium of solids prepared according to example 5 | | | |
|---|---|---|---|---|
| | Test | 5a | 5b | 5c | 5d |
| Molar Composition | $SiO_2$ in $NH_4{}^+$ exchanged Tixolex | 1 | 1 | 1 | 1 |
| | $Al_2O_3$ in $NH_4{}^+$ exchanged Tixolex | 0.07 | 0.07 | 0.07 | 0.07 |
| | Alkylamine | 2 Ethylamline* | 1 n-propyl-amine | 3 n-butyl-amine | 1 1,3-diamino-propane |
| | HF | 2 | 1 | 3 | 2.5 |
| | $H_2O$ | 10.5 | 30 | 10 | 2.5 |
| | Weight of engaged $NH_4{}^+$ exchanged Tixolex | 3.6 g | 9.9 g | 3.6 g | 3.6 g |
| | Weight of ferrierite germs | — | 0.13 g | — | 0.13 g |
| | Temperature °C. | 170 | 170 | 170 | 170 |
| | Time | 14 days | 17 days | 15 days | 10 days |

*Added as 70% ethylamine solution in water

EXAMPLE 6

Preparation, according to the invention, of ferrierites having a $SiO_2/Al_2O_3$ ratio higher than 70.

The two tests of example 6 show the possibility, by this method, to synthesize ferrierites whose $SiO_2/Al_2O_3$ ratio reaches or even exceeds the value 100.

Test 6a has been conducted with a reaction mixture containing 7g of silica-alumina (94.65% $SiO_2$, 2.5% $Al_2O_3$ and 2.7% $H_2O$), 9.17 ml of n-propylamine, 4.86 ml of 40% HF in water,. 56.5 ml of water and 0.13 g of ferrierite as germ. After reaction in autoclave for 15 days at 170° C., the obtained crystals are separated from the mother liquors, whose pH is close to 6.5, by filtration and washing. These crystals, as shown by X-ray diffraction diagram, consist exclusively of ferrierite. No other phase is detected either by X-ray diffraction or by microscopy. The crystals are roasted at 550° C. and chemically analyzed: their $SiO_2/Al_2O_3$ ratio is equal to 75. The fluorine content of the raw synthesis crystals is 1.25% by weight.

Test 6b has been conducted with a reaction mixture containing 3.6 g of precipitated Merck silica ($SiO_2/Al_2O_3$ ratio close to 560 as a result of the presence of alumina as impurity), 7.3 g of n-butylamine, 4.42 ml of 40% HF in water, 6g of water and 0.3 g of ferrierite used as germs. After reaction in autoclave for 15 days at 170° C., a solid is separated by filtration and washing with water. This solid comprises about 80% of ferrierite crystals and 20% of amorphous product which can be easily removed by settling after sonication. The so-purified ferrierite crystals have a $SiO_2/Al_2O_3$ ratio of 250.

EXAMPLE 7

Preparation, according to the invention, of ferrierites containing (Al, Ga), (Al, Fe) and (Al, B) as trivalent elements.

The four tests of example 7 show the possibility, by this method, to synthesize ferrierites containing trivalent elements other than aluminum, such for example as iron, gallium and boron.

The first reaction mixture (test 7a) contains 3.36 g of $HNO_3$-treated Tixolex (cf example 1) dispersed into a solution prepared with 20.6 g of water, 1.77 g of 40% HF in water, 3.33 ml of n-propylamine and 0.7 g of $GaCl_3$.

In the second reaction mixture (test 7b) $GaCl_3$ is replaced by 1.08 g of $Fe_2O_3$, $6H_2O$ and 0.12 g of ferrierite used as germs.

In the third reaction mixture (test 7c), the $GaCl_3$ amount (0.7 g) of mixture 7a is replaced by 0.07 g of the same compound.

In the fourth reaction mixture (test 7d), gallium is replaced by 0.6 g of $H_3BO_3$.

The reaction mixture of test 7a is heated in autoclave at 210° C. for 2 days. After cooling, the solid, filtered and washed, is formed of ferrierite crystals characterized by respective $SiO_2/Al_2O_3$ and $SiO_2/Ga_2O_3$ ratios of 28 and 35. The pH of the mother liquors, measured after cooling, is close to 8. The fluorine content of the raw synthesis solid is equal to 0.65% by weight. The X-ray diffraction spectrum is similar to that reported in Table 1.

The reaction mixture of test 7b is heated in autoclave at 170° C. for 12 days. After cooling, the pH is close to 7 and the solid, filtered and washed, is formed of ferrierite crystals with a small amount of amorphous product. After separation of the amorphous phase by settling (sonication) the chemical analysis shows that the ferrierite crystals contain 2.2% of $Al_2O_3$ and 1.75% of $Fe_2O_3$. The fluorine content of the synthesis raw crystals is 0.68% by weight and the X-ray diffraction spectrum is substantially identical to that shown in Table 1.

The reaction mixtures of tests 7c and 7d are treated as in test 7a. The obtained respective ferrierite crystals have a diffraction spectrum of the same type as that shown in Table 1. The chemical analysis of the product before roasting gives the following results:

Test 7c: $SiO_2/Al_2O_3 = 26$   $SiO_2/Ga_2O_3 = 380$   % F (by weight) = 0.90
Test 7d: $SiO_2/Al_2O_3 = 28$   $SiO_2/B_2O_3 = 45$    % F (by weight) = 0.70

EXAMPLE 8

Prepartion, according to the invention, of ferrierites of high silicium content, further containing gallium as trivalent element.

This example shows that it is possible to prepare ferrierites wherein silicium is substituted with other trivalent elements than aluminum.

25 ml of $Si(OC_2H_5)_4$, 2.1 g of $GaCl_3$ and 50 ml $H_2O$ are brought to reflux for 3 hours. After precipitation of the gallium-silicate gel, the latter is dried at 80° C., then finely crushed. The chemical analysis indicates a $SiO_2/Ga_2O_3$ molar ratio of 20 for this gel. A mixture is then formed whose molar composition is as follows: 1 $SiO_2$, 0.05 $Ga_2O_3$, 2 n-propyl amine, 2 HF, 20 $H_2O$. The engaged molar fraction amounts to 0.1 and the mixture contains 0.15 g of ferrierite crystals as germs. The initial pH is 7. The mixture, placed in an autoclave lined with PTFE, is brought to 200° C., for 6 days. During the heating step, the cylindrical autoclave revolves about an axis perpendicular to the cylinder axis, at a speed of 15 runs/minute. After cooling, the pH, measured in the reaction medium, is 7.5. The crystals, separated by filtration and washing, are formed of ferrierite having a $SiO_2/Ga_2O_3$ molar ratio of 24. The fluorine content of the raw synthesis solid is 0.55% by weight and the X-ray diffraction spectrum is substantially the same as shown in Table 1.

EXAMPLE 9

Preparation, according to the invention, of ferrierites used as catalysts for olefin oligomerization.

The ferrierite obtained by test 6a of example 6, whose $SiO_2/Al_2O_3$ molar ratio is 75, is roasted at 550° C. for 4 hours under a 20% air+80% nitrogen mixture (total flow rate of 10 liters $h^{-1}g^{-1}$).

At the end of this treatment, the solid is referenced Fer1; its fluorine content is 1.25% by weight.

The Fer1 H form ferrierite is treated in a $NH_4OH$ solution of 0.2N normality in an autoclave at 160° C. for 4 hours. After this treatment the zeolithe is washed on filter, then roasted at 550° C. for 4 hours under a 20% air+80% nitrogen mixture (total flow rate of 10 liters $h^{-1}g^{-1}$).

At the end of this treatment, the solid is referenced Fer2; its fluorine content is lower than 0.01% by weight.

EXAMPLE 10

Test of Fer1 and Fer2 ferrierites for propene oligomerization.

A propene oligomerization test has been conducted with 10 g of ferrierite (Fer1, Fer2) in a reactor of 65 cc capacity. The catalyst is placed between two beds of alpha alumina. Alpha alumina behaves as an inert solid in the oligomerization reaction.

Propene has been introduced in the following conditions:

| | |
|---|---|
| Temperature: | 330° C. |
| Pressure: | 4 MPa. |

In these operating conditions the propene conversion rates amount respectively to 89% and 75% for catalysts Fer1 and Fer2.

The liquid products withdrawn after conversion of the unconverted propene, for the two catalysts, had the following characteristics:

| | Fer1 | Fer2 |
|---|---|---|
| Density at 20° C. | 0.788 | 0.771 |
| Bromine number | 74 | 86 |
| ASTM Distillation | | |
| Initial point | 78° C. | 58° C. |
| 10% vol: | 143° C. | 123° C. |
| 30% vol: | 167° C. | 149° C. |
| 50% vol: | 210° C. | 195° C. |
| 70% vol: | 253° C. | 237° C. |
| 90% vol: | 298° C. | 283° C. |
| 95% vol: | 313° C. | 299° C. |
| Final point | 322° C. | 310° C. |

The distribution by number of carbon atoms, determined by mass spectrometry, is as follows:

| | Fer1 | Fer2 |
|---|---|---|
| C6 | 8.5% | 13.9% |
| C7 | 3.7% | 4.8% |
| C8 | 4.9% | 5.7% |
| C9 | 18.0% | 20.8% |
| C10 | 6.1% | 6.9% |
| C11 | 7.3% | 7.5% |
| C12 | 20.4% | 16.9% |
| C13 | 5.2% | 4.8% |
| C14 | 4.7% | 4.2% |
| C15 | 11.8% | 7.9% |
| C16 | 4.1% | 3.1% |
| C17 | 2.8% | 1.7% |
| C18+ | 2.5% | 1.8% |
| | 100.0% | 100.0% |

From the catalytic results, it appears that the presence of fluorine in larger amount in Fer1 than in Fer2 provides for improved performances in olefin oligomerization.

EXAMPLE 11

Oligomerization test for gallium, boron, aluminum and iron-containing ferrierites.

The propene oligomerization test has been performed according to example 10 except that ferrierite Fer1 of example 10 has been successively replaced by (Al, Ga) ferrierite, then by (Al, Fe) ferrierite, then by (Al, B) ferrierite of example 7, and finally by gallium ferrierite of example 8. The results are substantially as satisfactory as those obtained with ferrierite of example 10 as well for the conversion rate as for the selectivity.

What is claimed as the invention is:

1. In a catalytic olefin oligomerization process, the improvement which comprises employing as the catalyst a catalyst composition comprising a ferrierite of
    (a) the following formula:

$$M_{x/n}(T^{III}O_2)_x(Si^{IV}O_2)_{36-x}$$

where
- $T^{III}$ represents at least one element selected from the group consisting of boron ($B^{III}$), aluminum ($Al^{III}$), gallium ($Ga^{III}$) and iron ($Fe^{III}$);
- X ranges from 0.05 to 6.6;
- M is a compensation cation; and
- n is the valence of M;

(b) an X-ray diffraction diagram shown in Table 1 of the description;

(c) a fluorine content after synthesis ranging from about 0.01 to 1.6% by weight; and (d) a $Si^{IV}/T^{III}$ molar ratio of at least about 4.75;

and wherein said ferrierite is produced by the steps of:

(i) preparing a reaction mixture in aqueous solution at a pH lower than about 10, comprising at least one source of silicon oxide, one source of at least one oxide of trivalent metal T selected from the group consisting of boron, gallium, aluminum and iron, one source of fluorine ion F and at least one structurizing agent supplying nitrogen-containing organic cations, selected from the group consisting of primary and secondary aliphatic monoamines, diamines, triamines and ammonium cations derived by protonation of said mono-, di-, triamines, said agent having a total number of carbon and nitrogen atoms from 3 to 8, said mixture having a composition, in terms of molar ratios, ranging within the following intervals:

| | |
|---|---|
| $Si^{IV}/\Sigma T^{III}$ | at least 4.75 ($T^{III}$ = B, Al, Ga, Fe) |
| $F^-/Si^{IV}$ | 0.1–3 |
| Organic structurizing agent/$Si^{IV}$ | 0.1–4 |
| $H_2O/Si^{IV}$ | 4–200 |

(ii) maintaining said mixture at a heating temperature of at most 270° C., so as to obtain crystals, and (iii) roasting said crystals at a temperature higher than 400° C.

2. A process according to claim 1, characterized in that the $Si^{IV}/T^{III}$ molar ratio ranges from about 7 to about 500.

3. A process according to claim 1, said catalyst composition containing by weight:
   (a) at least 3% by weight of said ferrierite,
   (b) at most 97% by weight of a matrix selected from the group consisting of alumina, silica, magnesia, zirconia, titanium oxide, boron oxide, a clay and a mixture thereof.

4. A process according to claim 1, wherein said mixture in aqueous solution has a pH and a composition, in terms of molar ratios, ranging within the following intervals:

| | |
|---|---|
| PH | 4.5–9 |
| $Si^{IV}/\Sigma T^{III}$ | 4–150 ($T^{III}$ = B, Al, Ga, Fe) |
| $F^-/Si^{IV}$ | 0.25–2.5 |
| Organic structurizing agent | 0.25–2.5 |
| $H_2O/Si^{IV}$ | 6–80. |

5. A process according to claim 1, wherein the heating temperature of said reaction mixture is maintained within the range of 120°–260° C.

6. A process according to claim 1, wherein said crystals are roasted at a temperature within the range of about 500°–600° C.

7. A process according to claim 1, wherein said crystals are roasted in the presence of a molecular oxygen-containing gas.

8. A process according to claim 1, wherein at least a part of the original cations is replaced, by ion exchange, with a cation or mixture of cations selected from the group consisting of IIA, IIIA, IVA, IIB, IIIB, IVB, VIB, and VIII of the periodic classification of elements.

9. A process according to claim 1, said catalyst composition containing by weight:
   (a) at least 20% by weight of said ferrierite,
   (b) at most 20% by weight of a matrix selected from the group consisting of alumina, silica, magnesia, zirconia, titanium oxide, boron oxide, a clay and a mixture thereof.

* * * * *

UNITED STATES PATENT AND TRADEMARK OFFICE
CERTIFICATE OF CORRECTION

PATENT NO. : 4,982,046

DATED : January 1, 1991

INVENTOR(S) : Guth et al

It is certified that error appears in the above-identified patent and that said Letters Patent is hereby corrected as shown below:

Column 14, Claim 8, Line 34:

Reads: "group consisting of IIA, IIIA, IVA, IIB, IIIB, IVB," should read --group consisting of groups IIA, IIIA, IVA, IB, IIB, IIIB, IVB.--.

Signed and Sealed this

Thirtieth Day of June, 1992

*Attest:*

DOUGLAS B. COMER

*Attesting Officer*     Acting Commissioner of Patents and Trademarks